United States Patent
Diao et al.

(10) Patent No.: US 9,956,053 B2
(45) Date of Patent: May 1, 2018

(54) CANNULA WITH AN INTEGRATED ILLUMINATION FEATURE

(71) Applicant: NOVARTIS AG, Basel (CH)

(72) Inventors: Chenguang Diao, Irvine, CA (US); Alireza Mirsepassi, Irvine, CA (US); Ronald T. Smith, Irvine, CA (US); Michael J. Papac, North Tustin, CA (US)

(73) Assignee: NOVARTIS AG (CH)

( * ) Notice: Subject to any disclaimer, the term of this patent is extended or adjusted under 35 U.S.C. 154(b) by 288 days.

(21) Appl. No.: 15/061,754

(22) Filed: Mar. 4, 2016

(65) Prior Publication Data

US 2017/0252121 A1    Sep. 7, 2017

(51) Int. Cl.
| | |
|---|---|
| *A61B 90/30* | (2016.01) |
| *A61B 3/00* | (2006.01) |
| *A61F 9/007* | (2006.01) |
| *A61B 17/34* | (2006.01) |
| *B29C 65/48* | (2006.01) |

(Continued)

(52) U.S. Cl.
CPC ............ *A61B 90/30* (2016.02); *A61B 3/0008* (2013.01); *A61B 17/3415* (2013.01); *A61F 9/007* (2013.01); *B29C 65/14* (2013.01); *B29C 65/48* (2013.01); *A61B 2017/00526* (2013.01);
(Continued)

(58) Field of Classification Search
CPC .............................. A61B 90/30; A61B 3/0008
See application file for complete search history.

(56) References Cited

U.S. PATENT DOCUMENTS

| | | |
|---|---|---|
| 3,089,484 A | 5/1963 | Hett |
| 3,093,134 A | 6/1963 | Roehr |

(Continued)

FOREIGN PATENT DOCUMENTS

| | | |
|---|---|---|
| DE | 19957785 A1 | 6/2000 |
| EP | 0684016 A2 | 11/1995 |

(Continued)

OTHER PUBLICATIONS

International Search Report and Written Opinion of the International Searching Authority, International Application No. PCT/IB2016/051993, Not yet published, dated Jun. 16, 2016, 11 pages.

(Continued)

*Primary Examiner* — Christian Sevilla

(57) ABSTRACT

An illuminated microsurgical surgical instrument that allows for illumination of the interior of a body cavity during a surgical procedure is provided herein. The surgical instrument may include an elongate tubular member having a distal end for insertion through tissue, the elongate tubular member having an inner diameter, an outer diameter, and a wall thickness. A longitudinal slot extending from the distal end of the elongate tubular member is formed in the elongate tubular member. The surgical instrument further may include an optical fiber extending within the longitudinal slot toward the distal end of the elongate tubular member. The optical fiber may be affixed within the longitudinal slot by an adhesive. The optical fiber may be positioned such that a distal tip thereof is protected from damage by a distal edge of the elongate tubular member during insertion of the instrument into the body cavity.

20 Claims, 12 Drawing Sheets

(51) Int. Cl.
  *B29C 65/14*   (2006.01)
  *A61B 17/00*   (2006.01)
  *B29L 31/00*   (2006.01)

(52) U.S. Cl.
  CPC . *A61B 2090/306* (2016.02); *B29L 2031/7546* (2013.01); *B29L 2031/7548* (2013.01)

(56) References Cited

U.S. PATENT DOCUMENTS

| | | |
|---|---|---|
| 3,131,690 A | 5/1964 | Innis et al. |
| 3,385,553 A | 5/1968 | Braun |
| 3,439,157 A | 4/1969 | Myles |
| 3,910,677 A | 10/1975 | Becker et al. |
| 3,932,022 A | 1/1976 | Henning et al. |
| 3,981,709 A | 9/1976 | Kondo et al. |
| 3,990,453 A | 11/1976 | Douvas et al. |
| 4,168,707 A | 9/1979 | Douvas et al. |
| 4,200,106 A | 4/1980 | Douvas et al. |
| 4,597,030 A | 6/1986 | Brody |
| 4,607,622 A | 8/1986 | Fritch et al. |
| 4,641,912 A | 2/1987 | Goldenberg |
| 4,678,268 A | 7/1987 | Russo et al. |
| 4,693,244 A | 9/1987 | Daikuzono |
| 4,693,556 A | 9/1987 | McCaughan, Jr. |
| 4,733,933 A | 3/1988 | Pikulski |
| 4,781,703 A | 11/1988 | Walker et al. |
| 4,842,390 A | 6/1989 | Sottini et al. |
| 4,872,837 A | 10/1989 | Issalene et al. |
| 4,994,047 A | 2/1991 | Walker et al. |
| 4,995,691 A | 2/1991 | Purcell, Jr. |
| 5,037,174 A | 8/1991 | Thompson |
| 5,203,353 A | 4/1993 | Easley et al. |
| 5,217,456 A | 6/1993 | Narciso, Jr. |
| 5,219,350 A * | 6/1993 | Emerson ............... A61B 17/52 362/119 |
| 5,263,952 A | 11/1993 | Grace et al. |
| 5,312,393 A | 5/1994 | Mastel |
| 5,351,168 A | 9/1994 | Easley |
| 5,411,016 A | 5/1995 | Kume et al. |
| 5,425,730 A | 6/1995 | Luloh |
| 5,478,338 A | 12/1995 | Reynard |
| 5,620,639 A | 4/1997 | Stevens et al. |
| 5,630,809 A | 5/1997 | Connor |
| 5,651,783 A | 7/1997 | Reynard |
| 5,667,472 A | 9/1997 | Finn et al. |
| 5,695,492 A * | 12/1997 | Brown ................... A61B 90/20 606/4 |
| 5,716,320 A | 2/1998 | Buttermore |
| 5,725,514 A | 3/1998 | Grinblat et al. |
| 5,754,717 A | 5/1998 | Esch |
| 5,860,996 A | 1/1999 | Urban et al. |
| 6,080,143 A | 6/2000 | Connor |
| 6,206,823 B1 | 3/2001 | Kolata et al. |
| 6,217,456 B1 | 4/2001 | Jacob |
| 6,387,044 B1 | 5/2002 | Tachibana et al. |
| 6,428,553 B1 * | 8/2002 | Trese .................. A61F 9/00736 606/16 |
| 6,454,744 B1 | 9/2002 | Spohn et al. |
| 6,939,341 B2 | 9/2005 | Vijfvinkel |
| 7,473,249 B2 | 1/2009 | Scheller et al. |
| 7,593,778 B2 | 9/2009 | Chandran et al. |
| 7,766,904 B2 | 8/2010 | McGowan, Sr. et al. |
| 7,881,573 B2 | 2/2011 | Eberle et al. |
| 7,896,838 B2 | 3/2011 | Devega |
| 7,901,353 B2 | 3/2011 | Vayser et al. |
| 8,496,862 B2 | 7/2013 | Zelkovich et al. |
| 8,900,139 B2 | 12/2014 | Yadlowsky et al. |
| 8,968,347 B2 | 3/2015 | McCollam |
| 9,066,678 B2 | 6/2015 | Auld et al. |
| 9,402,643 B2 | 8/2016 | Auld et al. |
| 2001/0056278 A1 | 12/2001 | Nield et al. |
| 2002/0035425 A1 | 3/2002 | Deguchi et al. |
| 2002/0123744 A1 | 9/2002 | Reynard |
| 2004/0215065 A1 | 10/2004 | Setten |
| 2005/0080384 A1 | 4/2005 | Green, Jr. |
| 2005/0135776 A1 | 6/2005 | Vijfvinkel |
| 2005/0154379 A1 | 7/2005 | McGowan, Sr. et al. |
| 2005/0245916 A1 | 11/2005 | Connor |
| 2006/0135973 A1 | 6/2006 | Hawkins et al. |
| 2006/0211918 A1 | 9/2006 | Lieponis |
| 2007/0179430 A1 | 8/2007 | Smith et al. |
| 2007/0255264 A1 | 11/2007 | Hickingbotham |
| 2008/0108981 A1 | 5/2008 | Telfair et al. |
| 2008/0147018 A1 | 6/2008 | Squilla et al. |
| 2008/0179792 A1 | 7/2008 | Kurimoto et al. |
| 2008/0255545 A1 | 10/2008 | Mansfield et al. |
| 2009/0030406 A1 | 1/2009 | Hickingbotham |
| 2009/0131931 A1 | 5/2009 | Lee et al. |
| 2009/0135280 A1 | 5/2009 | Johnston et al. |
| 2009/0163897 A1 | 6/2009 | Skinner |
| 2009/0182313 A1 | 7/2009 | Auld et al. |
| 2009/0221991 A1 | 9/2009 | Lieponis |
| 2010/0026207 A1 | 2/2010 | Facchini et al. |
| 2010/0081875 A1 * | 4/2010 | Fowler ............... A61B 1/00149 600/114 |
| 2010/0145284 A1 | 6/2010 | Togashi |
| 2010/0228083 A1 | 9/2010 | Mirza et al. |
| 2010/0228085 A1 | 9/2010 | Mirza et al. |
| 2011/0130779 A1 | 6/2011 | Mirza et al. |
| 2011/0282160 A1 | 11/2011 | Bhadri et al. |
| 2011/0319839 A1 | 12/2011 | Del Vecchio |
| 2012/0035425 A1 | 2/2012 | Schaller |
| 2012/0041461 A1 | 2/2012 | McCollam |
| 2012/0203075 A1 | 8/2012 | Horvath |
| 2012/0238830 A1 | 9/2012 | Vukeljic et al. |
| 2012/0283523 A1 | 11/2012 | Yadlowsky et al. |
| 2012/0296173 A1 | 11/2012 | Stocks et al. |
| 2013/0012783 A1 | 1/2013 | Vayser et al. |
| 2013/0079598 A1 | 3/2013 | Auld et al. |
| 2013/0282031 A1 | 10/2013 | Woodard, Jr. et al. |
| 2014/0100426 A1 | 4/2014 | Barbour |
| 2014/0121469 A1 | 5/2014 | Mccollam et al. |
| 2014/0210116 A1 | 7/2014 | Schaller |
| 2014/0357957 A1 | 12/2014 | Bhadri et al. |
| 2014/0379054 A1 | 12/2014 | Cooper et al. |
| 2015/0011838 A1 | 1/2015 | Auld et al. |
| 2015/0011839 A1 | 1/2015 | Auld et al. |
| 2016/0113722 A1 | 4/2016 | Heeren |

FOREIGN PATENT DOCUMENTS

| | | |
|---|---|---|
| GB | 1207229 A | 9/1970 |
| GB | 1349881 A | 4/1974 |
| JP | H10234665 | 9/1998 |
| JP | 2000245740 A2 | 9/2000 |
| JP | 2001079010 A2 | 3/2001 |
| JP | 2006325973 A2 | 12/2006 |
| JP | 2009519766 T2 | 5/2009 |
| JP | 2009148550 A2 | 7/2009 |
| PL | 166358 B1 | 5/1995 |
| WO | 0139705 A1 | 6/2001 |
| WO | 0248017 A1 | 6/2002 |
| WO | 2004002337 A1 | 1/2004 |
| WO | 2007081474 A2 | 7/2007 |
| WO | 08139982 A1 | 11/2008 |
| WO | 2008139982 A1 | 11/2008 |
| WO | 2009091462 A1 | 7/2009 |
| WO | 2012083247 A1 | 6/2012 |

OTHER PUBLICATIONS

International Search Report and Written Opinion of the International Searching Authority, International Application No. PCT/2013/067083, dated Jan. 16, 2014, 9 pages.
PCT International Preliminary Report on Patentability and Written Opinion, Application No. PCT/US2013/67083, Publication No. WO/2014/070664, dated May 5, 2015, 8 pages.
International Search Report for PCT/US2008/086119, Publication No. WO2009/091462, dated Mar. 30, 2009, 2 pages.
PCT International Preliminary Report on Patentability and Written Opinion of the International Searching Authority, International Application No. PCT/US2008/086119, dated Jul. 20, 2010, 7 pages.

(56) References Cited

OTHER PUBLICATIONS

PCT International Preliminary Report on Patentability and Written Opinion, PCT/US2011/046942, dated Feb. 12, 2013, 6 pages.
International Search Report for PCT/US2011/046942, dated Nov. 15, 2011, 4 pages.
International Search Report for PCT/US2011/047262, dated Dec. 12, 2011, 2 pages.
Supplementary European Search Report for PCT/US2011/047262, dated Oct. 9, 2013, 8 pages.
Calhoun, The Roto-Extractor in Pediatric Ophthalmology, Tr. Am. Ophth. Soc., vol. LXXIII, pp. 292-305, 1975.
Carron, Fiber Optics in Computer Screens to Save Energy, Feb. 22, 2012, 2 pages, retrieved Oct. 29, 2015 from http://phys.org/news/2012-02-fiber-optics-screens-energy.html.
Chalam, et al., Illuminated Curved Vitrectomy Probe for Vitreoretinal Surgery, Ophthalmic Surgery, Lasers and Imaging, Nov./Dec. 2007—vol. 38 Â—Issue 6: 525-526.
Douvas, Microsurgical Roto-Extractor Instrument for Vitrectomy, Mod. Probl. Ophthal., vol. 15, pp. 253-260 (Karger, Basel 1975).
Fisher et al., Inexpensive Illuminated Vitrectomy Cutter, The Journal of Retinal and Vitreous Diseases, Dec. 2003, vol. 23, Issue 6, p. 891.
European Search Report for Application No. 13851516.8, Publication No. EP2861125, dated Apr. 22, 2015, 6 pages.
International Search Report and Written Opinion, PCT/US2015/054426, dated Jan. 8, 2016, 15 pages.

\* cited by examiner

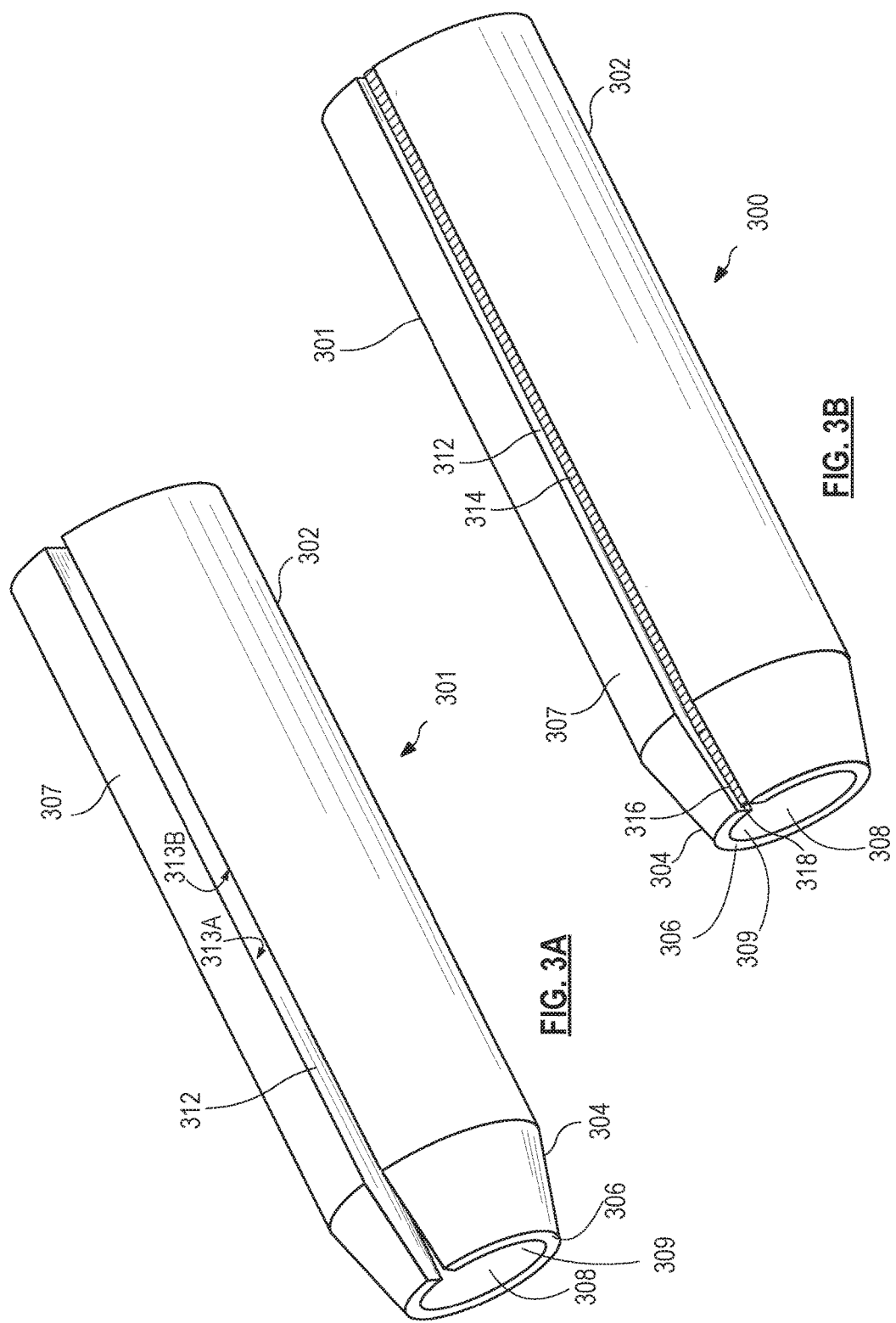

CANNULA WITH AN INTEGRATED ILLUMINATION FEATURE

TECHNICAL FIELD

The present disclosure is directed to devices for illumination and methods and systems associated therewith and, more particularly, to devices, systems, and methods for illuminating a body cavity.

BACKGROUND

Intraocular procedures are commonly performed to treat many serious conditions of the posterior segment of the eye. For example, vitreoretinal procedures may treat conditions such as age-related macular degeneration (AMD), diabetic retinopathy, diabetic vitreous hemorrhage, macular hole, retinal detachment, development or presence of an epiretinal membrane (a growth condition also referred to as macular pucker), cytomegalovirus (CMV) retinitis, and many other ophthalmic conditions.

A surgeon may observe intraocular or other intra-cavity procedures through a microscope and special lenses designed to provide a clear image of the interior of the cavity. Access to cavities is provided through one or more incisions that may be formed through the sclera. A surgeon inserts microsurgical instruments through the incisions, such as a light source to illuminate inside the eye, an infusion line to introduce infusion fluid into the eye, and instruments to cut and remove the vitreous body or to perform other surgical operations. A separate incision may be provided for each microsurgical instrument when using multiple instruments simultaneously.

During such surgical procedures, proper illumination of the inside of the eye is important. Typically, an illuminator is inserted into an incision to provide illumination into the eye.

SUMMARY

The present disclosure is directed to exemplary illuminated microsurgical instruments and to methods of fabrication such instruments. The instruments may include an optical fiber for delivering light to a surgical site.

Exemplary surgical systems are provided herein. An exemplary surgical system may include a surgical instrument having an elongate tubular member with a distal end for insertion through eye tissue to provide access to an interior of an eye. The elongate tubular member may have an inner surface, an outer surface, and a wall thickness therebetween and may include a longitudinally-extending slot or opening. The longitudinally-extending slot may extend from the distal end of the elongate tubular member in a proximal direction. The surgical instrument may also include an optical fiber disposed within the longitudinally-extending slot, which may extend toward the distal end of the elongate tubular member. The optical fiber may be affixed to the elongate tubular member within the longitudinally-extending slot. This exemplary surgical instrument may provide the required illumination during a surgical procedure while protecting the optical fiber tip from damage during instrument insertion.

Exemplary methods of forming such surgical instruments are also provided herein. An exemplary method may include inserting a pin into a lumen extending through an elongate tubular member. The elongate tubular member may include an outer surface and an inner surface that defines an inner diameter of the lumen. The outer diameter of the pin may match the inner diameter of the elongate tubular member. An optical fiber may be positioned within a longitudinal opening or a slot formed in the elongate tubular member. The longitudinal opening may connect the inner and outer surfaces of the elongate tubular member. The optical fiber may be affixed within the longitudinal opening, and the pin may be removed from the lumen of the elongate tubular member.

Exemplary methods of forming a trocar cannula for use in an ophthalmic surgical procedure are also provided herein. A pin may be inserted into a lumen that extends through an elongate tubular member. The elongate tubular member may include a longitudinal opening formed therein. An optical fiber may be positioned within the longitudinal opening formed in the elongate tubular member. Additionally, a tube may be placed over the elongate tubular member, such that the tube covers a portion of the elongate tubular member and a portion of the elongate optical fiber. The optical fiber may be affixed within the longitudinal opening, and, thereafter, the pin may be removed from the lumen of the elongate tubular member.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the accompanying drawings and the following detailed description.

BRIEF DESCRIPTION OF THE DRAWINGS

The accompanying drawings illustrate implementations of the devices and methods disclosed herein and together with the description, serve to explain the principles of the present disclosure.

FIGS. 3A and 3B are perspective views of an exemplary cannula.

Figure 1:
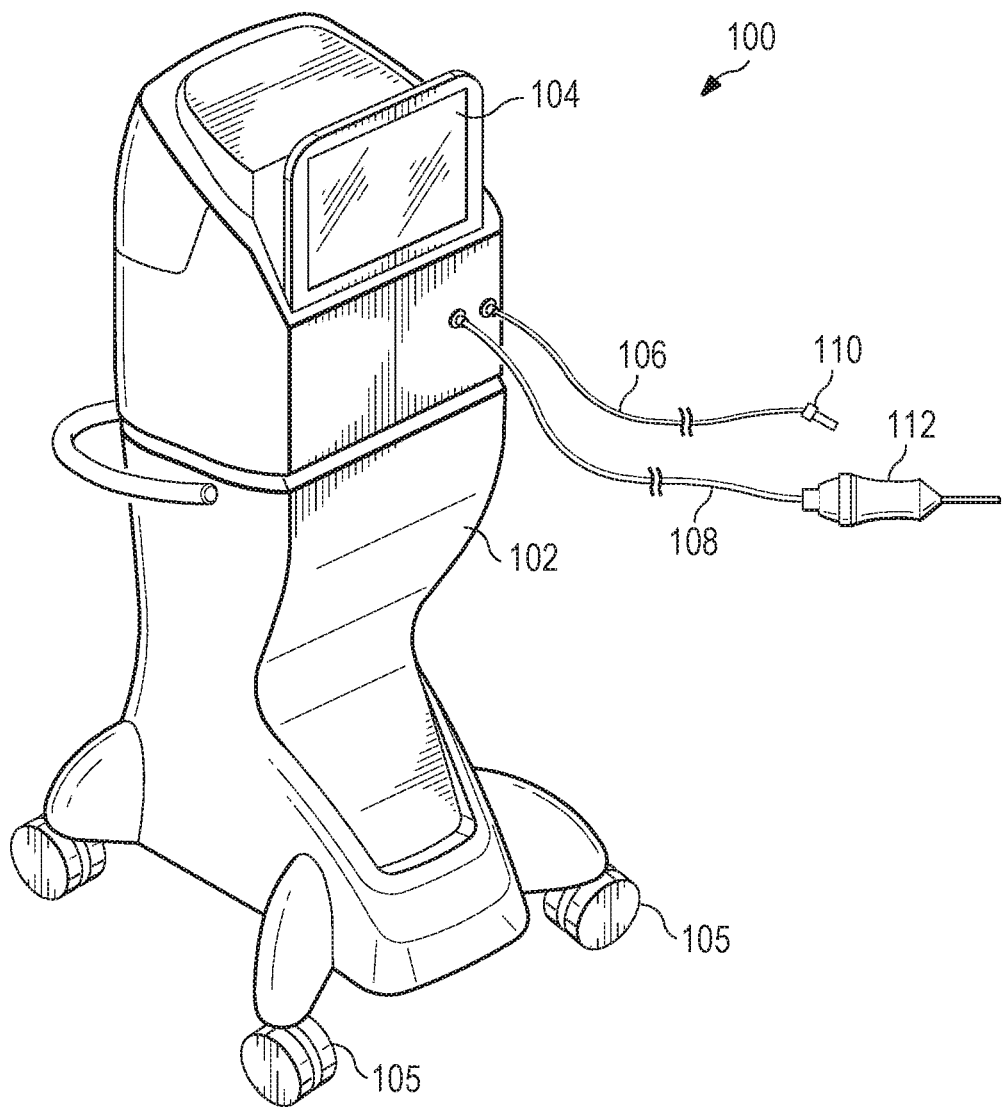
FIG. 1 illustrates a perspective view of an exemplary surgical system.

The accompanying drawings may be better understood by reference to the following detailed description.

DETAILED DESCRIPTION

For the purposes of promoting an understanding of the principles of the present disclosure, reference will now be made to the implementations illustrated in the drawings, and specific language will be used to describe the same. It will nevertheless be understood that no limitation of the scope of the disclosure is intended. For example, some more specific implementations of the present disclosure are directed to illuminated instruments usable in ophthalmic surgical treatments; however, the application of the principles of the present disclosure to illuminated instruments usable in other surgical treatments is within the scope of this disclosure. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or operations described with respect to one implementation may be combined with the features, components, and/or operations described with respect to other implementations of the present disclosure. For simplicity, in some instances the same reference numbers are used throughout the drawings to refer to the same or like parts.

The present disclosure is directed to surgical cannula devices that provide an opening into a body cavity. One or more surgical tools may be inserted through such a surgical cannula device in order to perform a surgical treatment within the cavity. The surgical cannula device may provide illumination within a body cavity during the treatment performed therein without requiring a separate incision to be made specifically for the illumination source. Illumination may be provided through an optical fiber extending along a length of the surgical cannula device and into the body cavity. In some examples, the body cavity is the vitreous chamber of an eye.

For example, a vitrectomy procedure may be performed to remove vitreous from the vitreous chamber of the eye of a patient. A vitrectomy cutter may be used to remove the vitreous. Rather than forming separate incisions in the eye of the patient, one for each of the vitrectomy cutter and an illumination device, the optical fiber may be positioned along a portion of a cannula device through which the vitrectomy cutter may be introduced into the vitreous chamber. The optical fiber may have a distal tip from which light is introduced or emitted into the vitreous chamber of the eye. The illumination provided by the cannula device may improve visualization of the vitreous contained within the vitreous chamber. Visualizing the vitreous and other portions of the eye may enable a user, such as a surgeon or other medical professional, to perform the surgical procedure efficiently and accurately, while minimizing trauma to other tissues in the eye, such as by eliminating a separate wound in the eye to accommodate a separate illumination device.

In some implementations, an example cannula may include a longitudinal opening or a slot (generally referred to as "longitudinal slot") extending a length thereof, such as an entire length of the cannula or along a portion of an entire length of the cannula. For example, in some instances, a longitudinal slot may be formed along a substantial portion of the entire length of the cannula or less than a substantial length of the cannula. In some implementations, the longitudinal slot may extend through a wall of the cannula, from an inner surface of the wall to an outer surface of the wall. Thus, the longitudinal slot may extend through the entire wall thickness of the cannula and provide communication between an interior and exterior of the cannula. An optical fiber may be positioned within the longitudinal slot. In some instances, the longitudinal slot may extend along the cannula in a direction substantially parallel to the longitudinal axis of the cannula. In other instances, a portion of the longitudinal slot may have a twist that forms a spiral around at least a portion of the cannula or may have some other non-longitudinally extending configuration.

The optical fiber may extend within the longitudinal slot and may be affixed therein. For example, an adhesive, such as an epoxy, may be used to affix the optical fiber within the slot. In implementations where the longitudinal slot extends completely through a wall of the cannula, the optical fiber may be completely imbedded within the longitudinal slot. This may protect the fragile tip of the optical fiber from damage during insertion of the cannula into the eye. Furthermore, with the optical fiber imbedded within the longitudinal slot, the gauge size of the cannula can remain small, minimizing the size of any required incision. In some implementations, to better visualize the vitreous which is generally clear, the optical fiber may be configured to concentrate the emitted light in the near field and diffuse the emitted light in the far field, thereby preventing "hot spots" from forming on the retina. In some instances, the distal end of the optical fiber may be positioned near the distal end of the cannula. With the distal end of the optical fiber positioned near the distal end of the cannula, the resulting illumination may provide better visualization of the interior of the eye, for example.

FIG. 1 illustrates an example surgical system 100. The surgical system 100 includes a console 102 and an associated display 104. The display 104 may display, for example, data relating to system operation and/or system performance during a surgical procedure. In some implementations, the console 102 may be mobile. For example, in some implementations, the console 102 may include wheels or casters 105 to facilitate movement of the console 102. In other implementations, the console 102 may not include wheels or casters. The console 102 may include a one or more subsystems that enable a surgeon to perform a variety of surgical procedures, such as ophthalmic surgical procedures. For example, the console 102 may include an illumination subsystem with a light source producing light that can be directed into a body cavity to allow a surgeon to operate therein. In some instances, the light source may include a halogen tungsten lamp, a high pressure arc lamp (e.g., using metal-halides or xenon), a light emitting diode (LED), a laser, or other light source. Light generated by the light source may be transmitted into the eye via the optical fiber. In some implementations, the light may pass through one or more optical elements, such as, for example, one or more lenses, mirrors, and/or attenuators, before or after entering the optical fiber.

As shown in FIG. 1, an access instrument, generally referred to as a cannula 110, is coupled to the console 102 and to the illumination subsystem therein by an illumination line 106. The illumination line 106 conducts light to the cannula 110. The light is introduced into the eye of a patient during an ophthalmic procedure. In some implementations, the illumination line 106 may include an optical fiber or portion thereof and/or an optical cable or portion thereof. The cannula 110 may be used to make or to open an incision through the wall of a body cavity, for example, through the sclera of an eye. In some instances, the cannula 110 may be inserted into an incision made by a user, such as a surgeon or other medical professional, using another surgical tool. The cannula 110 may include a lumen through which a surgeon may insert one or more surgical tools in order to perform a surgical procedure within the cavity.

An exemplary surgical tool, which is illustrated as a handpiece 112, may be coupled to the console 102 and may form a part of the surgical system 100. The handpiece 112 represents any number of surgical devices, including, for example, a vitrectomy probe, an illumination probe, an aspiration probe, an irrigation probe, a phacoemulsification device, a diathermy probe, or other types of devices. In the illustrated implementation, the handpiece 112 is a vitrectomy probe used to remove vitreous from an eye. The handpiece 112 may be coupled to one or more subsystems included in the console 102. For example, the handpiece 112 may be coupled to a vitrectomy subsystem that controls a pump and/or a vacuum for use in the removal of vitreous. The vitrectomy subsystem may also provide power to the handpiece 112 and control operation of the handpiece 112. In some implementations, the handpiece 112 may be a vitreous cutter, such as, for example, an oscillating vitreous cutter. In some implementations of the surgical system 100, the cannula 110 and the handpiece 112 may be coupled to different consoles, rather than to a single console 102 as illustrated. The system 100 may be used in various ophthalmic procedures, such as an anterior segment procedure, a posterior segment procedure, a vitreoretinal procedure, a vitrectomy procedure, a cataract procedure, and/or other procedures.

Figure 2:
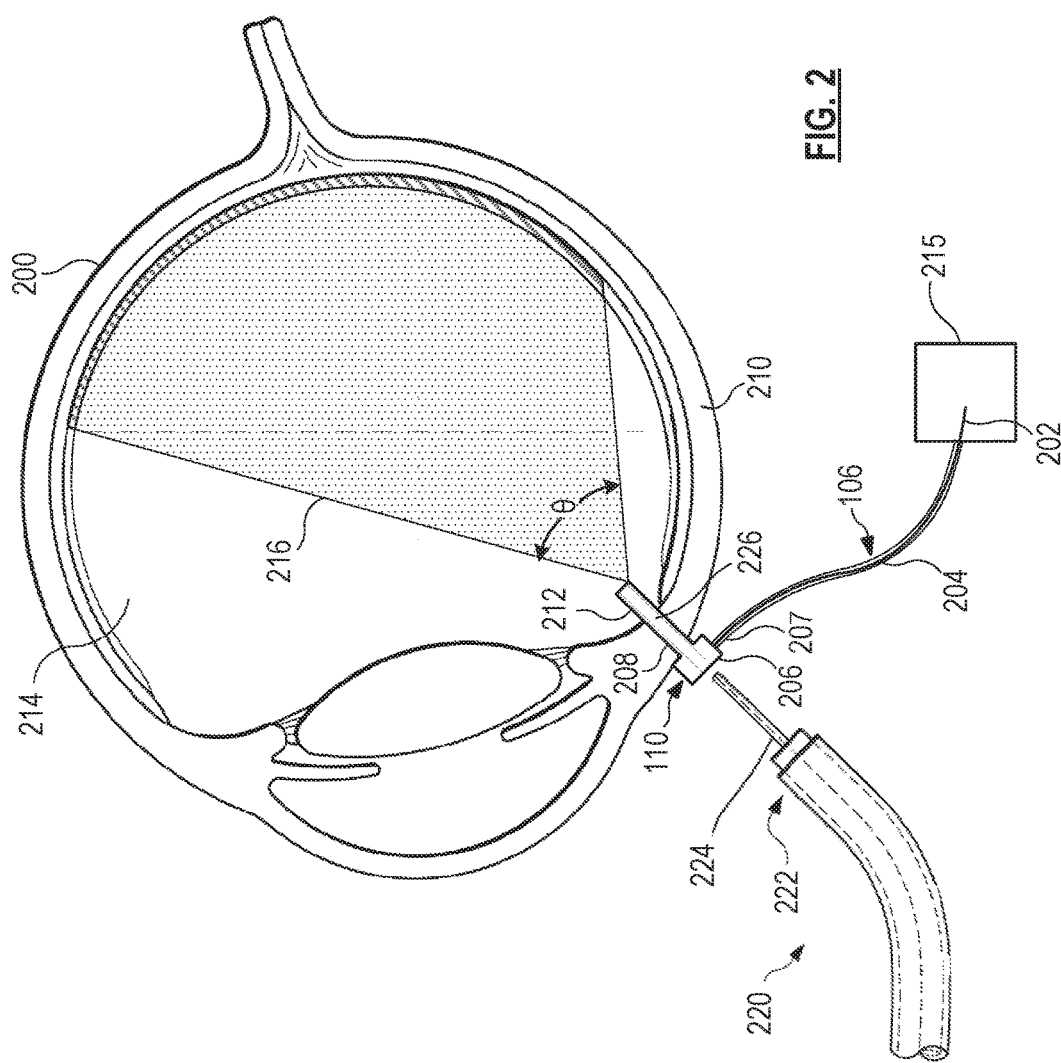
FIG. 2 is an illustration of an exemplary cannula inserted through the sclera of an eye.

FIG. 2 illustrates an example application of a portion of the surgical system 100 of FIG. 1 during an ophthalmic procedure. FIG. 2 shows the example cannula 110 in situ in an eye 200. As can be seen, the cannula 110 includes an elongate tubular member 208 that is coupled to a hub 206 at one end. In some implementations, the hub 206 may be secured to a needle or trocar used to facilitate insertion of the elongate tubular member 208 through the sclera 210. The needle may be removed after the cannula 110 is in position. In some implementations, the hub 206 may be a flange of the cannula 110. In some instances, a distal end 212 of the elongate tubular member 208 may be tapered to provide a sharpened edge that may be more easily inserted through the sclera 210. The elongate tubular member 208 may be formed from a rigid material, such as a rigid polymer or a metal (e.g., stainless steel, titanium, etc.), so that the cannula 110 can be pushed through the incision made in the sclera 210 of the eye 200. The cannula 110 may include a central lumen 226 extending therethrough. The central lumen 226 provides communication between the exterior of the eye 200 and the interior of the eye 200. Further, the central lumen 226 provides a conduit through which an instrument may be introduced into the eye 200.

The illumination line 106 may be or include an elongate member 204 that defines a passage therethrough. In some instances, the elongate member 204 may be formed of a flexible material. Thus, the illumination line 106 may be flexible. An optical fiber 202 may extend through the passage of the elongate member 204. In some implementations, the flexible elongate member 204 may be a cover, sheath, coating, or other protector formed on or surrounding the optical fiber 202. The elongate member 204 may be formed of any suitable material, including, without limitation, medical-grade tubing, such as plastic materials, elastomeric materials, and/or other desired or suitable materials.

In some implementations, the elongate member 204 is formed of a silicone material. The optical fiber 202 may be disposed within a lumen of the elongate member 204. In some implementations, the optical fiber 202 is freely movable within the lumen of the elongate member 204. In other implementations, the optical fiber 202 is directly or indirectly coupled to a lumen wall of the elongate member 204, such as by mechanical attachment, adhesive, and/or in any other desired or suitable manner.

A distal end 207 of the elongate member 204 may be secured to the hub 206 of the cannula 110 to enable a user, such as a surgeon or other medical professional, to more easily handle the cannula 110 while positioning the elongate tubular member 208 of the cannula 110 through the wall of a body cavity. In some implementations, the elongate member 204 may be coupled to a proximal end of the elongate tubular member 208 without being coupled to the hub 206. In some implementations the elongate member 204 may be coupled to both the proximal end of the elongate tubular member 208 and the hub 206.

A portion of the optical fiber 202 may extend along a length of the elongate tubular member 208, as discussed in more detail below. A proximal end of the optical fiber 202 may be optically coupled to a light source 215, and light produced by the light source 215 may be transmitted into and through the optical fiber 202. The light source 215 may be configured to output any desired or suitable type of light. The light source 215 may include an incandescent light bulb, a halogen light bulb, a metal halide light bulb, a xenon light bulb, a mercury vapor light bulb, a light emitting diode (LED), a laser, such as, for example, a white laser, a combination thereof, and/or another light source. In some instances, the light source 215 forms part of a surgical console, such as console 102. In other instances, the light source 215 may be separate from a surgical console. Thus, in some instances, the light source 215 may be or form part of a separate component. Thus, with the distal end 212 of the elongate tubular member 208 positioned within an interior of the eye 200 (such as the vitreous chamber 214), light produced by the light source 215 and transmitted through the optical fiber 202 is communicated into the eye 200 to provide illumination therein.

Referring to FIG. 2, the illumination 216 defines an illumination angle θ. The optical fiber 202 may be configured such that the illumination angle θ results in illumination to a wide field of view within the eye 200. In this manner, illumination provided by the optical fiber 202 may sufficiently illuminate the surgical field so as to avoid the need for another source of illumination.

FIG. 2 also shows a surgical tool 220. As illustrated, the surgical tool 220 is an infusion line configured to introduce a fluid into the interior of the eye 200, such as, for example, the vitreous chamber 214. However, the scope of the disclosure is not so limited. Rather, the surgical tool 220 may be or include any other type of tool. Example surgical tools may include a vitrectomy probe, an aspiration line, forceps, scissors, scraper, an optical coherence tomography (OCT) probe, laser probe, or any other desired tool, probe, or instrument.

The surgical tool 220 includes a distal end 222 that has an infusion tube 224 extending therefrom. The infusion tube 224 has a diameter sufficiently sized to pass through the central lumen 226 of the cannula 110. With the infusion tube 224 positioned within the central lumen 226 of cannula 110, the illumination 216 may enable a user to better assess the fluid flow from the infusion tube 224 into the vitreous chamber 214, for example. In some implementations, the illumination angle θ or another quality of the light may be affected if a portion of the surgical tool 220 enters into or otherwise interferes with the illumination emitted by at the distal end 212 of the elongate tubular member 208 from the optical fiber 202.

In some implementations, the optical fiber 202 may be coupled to the hub 206 in such a way that the optical fiber 202 may bend away from a longitudinal axis of the elongate tubular member 208 to facilitate insertion of the surgical tool 220 through the central lumen 226. In some implementations, a coupling joint may be used to couple the flexible elongate member 204 to the cannula 110. While FIG. 2 illustrates the flexible elongate member 204 and the optical fiber 202 as connecting to the hub 206 at approximately a 90 degree angle relative to the elongate tubular member 208, the flexible elongate member 204 may be connected with the hub 206 at some other angle. For example, in some implementations, the optical fiber 202 may connect to the hub 206 such that the optical fiber 202 is parallel to the elongate tubular member 208. In other instances, the optical fiber 202 may connect to the hub 206 such that the optical fiber 202 forms an oblique angle relative to the longitudinal axis of the elongate tubular member 208.

Figures 3C, 3D:
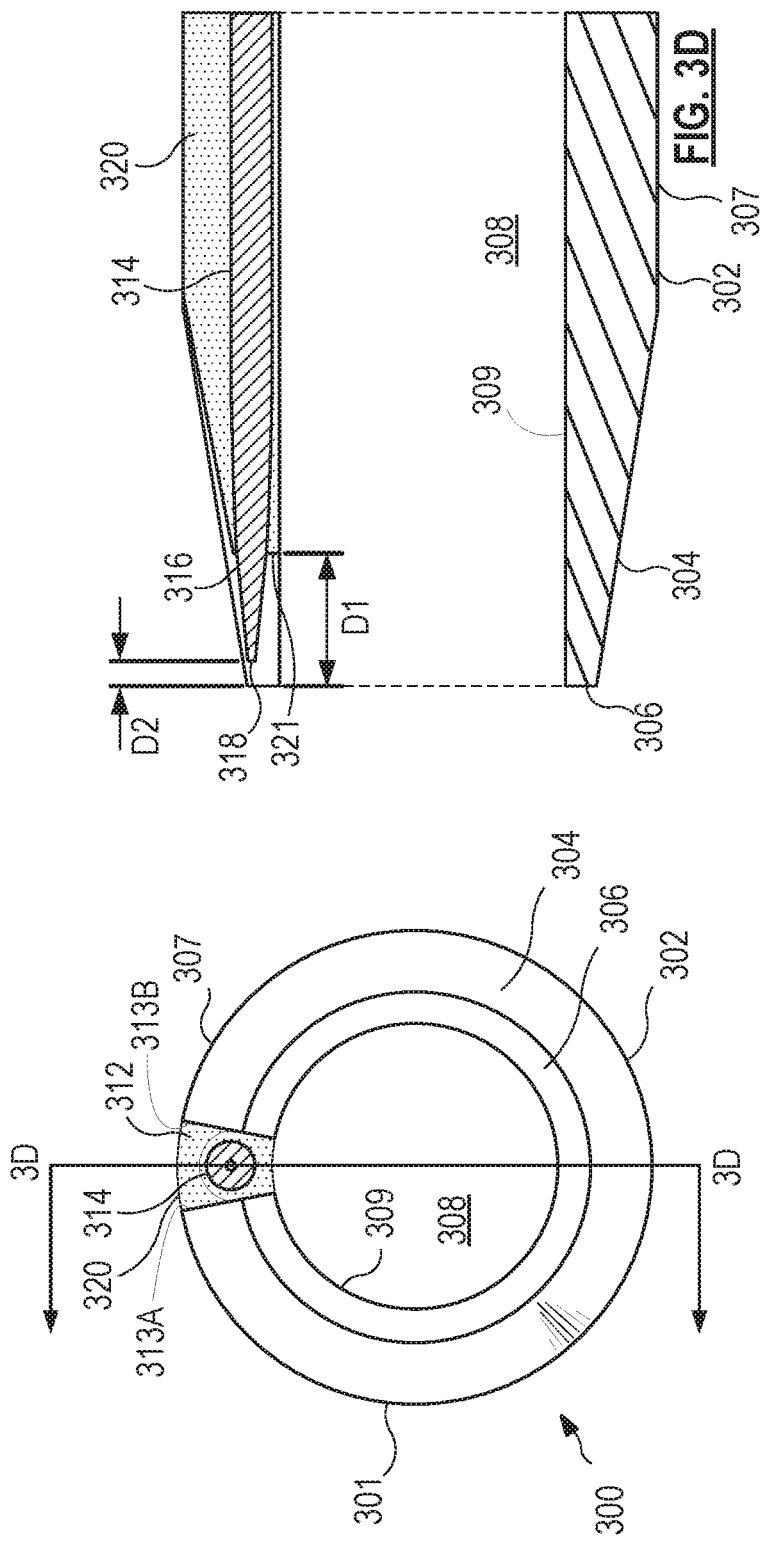
FIG. 3C is an end view of the exemplary cannula of FIGS. 3A and 3B.
FIG. 3D is a cross-sectional view of a distal portion of the exemplary cannula of FIGS. 3A and 3B along the line 3D-3D of FIG. 3B.

FIGS. 3A, 3B, 3C, and 3D show details of an example cannula device 300 according to aspects of the present disclosure. The cannula device 300 includes a cannula 301 and an optical fiber 314. FIGS. 3A and 3B are perspective views of the example cannula 300 having a longitudinal slot 312. FIG. 3B shows an optical fiber 314 disposed in the longitudinal slot 312.

The cannula 301 may include an elongate tubular member 302 that is substantially circular in cross-section and has a substantially cylindrical outer surface 307 and a substantially cylindrical inner surface 309. The cannula 301 may include a tapered section 304 at a distal end 306 of the elongate tubular member 302. In some implementations, the tapered section 304 may include a sharp edge to facilitate insertion through the sclera of an eye, such as the sclera 210 of the eye 200 shown in FIG. 2. The cannula 301 includes a lumen 308 extending a length of the elongate tubular member 302. In some implementations, the lumen 308 may extend the entire length of the elongate tubular member 302. The lumen 308 may be centered within the elongate tubular member 302 in some implementations. The elongate tubular member 302 of cannula 301 includes the longitudinal slot 312. In some implementations, the longitudinal slot 312 may extend along the entire length of the elongate tubular member 302, as depicted in FIGS. 3A and 3B. In other implementations, the longitudinal slot 312 may extend along a portion of the length of the elongate tubular member 302.

As illustrated in FIGS. 3A and 3B, the longitudinal slot 312 may extend from the outer surface 307 of the elongate tubular member 302 to the inner surface 309 of the elongate tubular member 302. Accordingly, the longitudinal slot 312 may extend through an entire wall thickness of the elongated tubular member 302 thereby forming a through-opening that extends axially along the elongate tubular member 302.

The longitudinal slot 312 may be formed in the elongate tubular member 302 by any of many different fabrication techniques. For example, the longitudinal slot 312 may be formed by laser cutting, milling, electrical discharge manufacturing, or using any other method or technique. The longitudinal slot 312 includes opposing walls 313A and 313B. Depending on the manufacturing process and associated process parameters used to generate the longitudinal slot 312, the opposing walls 313A and 313B may be parallel to each other or may be angled relative to each other, such that the radially outer portions of the opposing walls 313A and 313B may be closer together or further apart than the radially inner portions of the opposing walls 313A and 313B. The opposing walls 313A and 313B may be seen more easily in FIG. 3C. The longitudinal slot 312 may be sized to fully accommodate the optical fiber 314 therein, as described in greater detail below.

The optical fiber 314 may be sized to fit within the longitudinal slot 312. In some implementations, the optical fiber 314 may range in diameter from about 20 microns to about 50 microns. In other implementations, the optical fiber 314 may be about 30 microns to about 40 microns in diameter. The wall of the elongate tubular member 302, defined between the inner surface 309 and the outer surface 307, may have a thickness ranging from about 30 microns to about 50 microns depending on the gauge size of the cannula 301. In some implementations, the cannula 301 may be a 25-gauge needle. Because of the longitudinal slot 312 and the thickness of the wall of the elongate tubular member 302, the optical fiber 314 shown in FIG. 3B may not protrude beyond the outer surface 307 of the elongate tubular member 302. Further, in some implementations, the optical fiber 314 may not protrude radially inwardly beyond the inner surface 309. Thus, in some implementations, the optical fiber 314 may disposed within the longitudinal slot 312 may be entirely contained between the region bounded by the outer surface 307 and the inner surface 309. This may be observed in FIGS. 3C and 3D.

FIG. 3C is an end view of the cannula device 300, while FIG. 3D is a longitudinal cross-sectional view of the cannula device 300 along the line 3D-3D of FIG. 3C. As shown in FIGS. 3C and 3D, the optical fiber 314 may be affixed within the longitudinal slot 312 between opposing walls 313A and 313B. In some implementations, the optical fiber may be affixed within the longitudinal slot 312 by an adhesive 320. In some instances, the distal end 321 of the adhesive 320 may be offset from a distal end 318 of the optical fiber 314 by a distance equal to the difference of D1 and D2 (i.e., the offset distance of the distal end 321 of the adhesive 320 and distal end 318 of the optical fiber 314=D1-D2). The offset between the distal end 318 of the optical fiber 314 and the distal end 321 of the adhesive 320 may leave at least a portion of a tapered distal section 316 of the optical fiber 314 uncovered by the adhesive 320.

Because the longitudinal slot 312 extends from the outer surface 307 to the inner surface 309, the cannula 301 may form a nearly closed C-shape when viewed in cross-section. As shown in FIGS. 3C and 3D, in some implementations, the optical fiber 314 does not protrude from the longitudinal slot 312 in the tapered section 304 or along a length the cylindrical portion of the elongate tubular member 302. In such implementations, the size of the diameter of the optical fiber 314 is equal to or smaller than the wall thickness of the elongate tubular member 302.

In some implementations, the distal end 318 of optical fiber 314 may be offset from the distal end 306 of the elongate tubular member 302 by an offset distance D2. In some implementations, the distance D2 may be less than the distance D1. For example, in some implementations, the distance D2 may range from less than about one micron to about five microns. In other implementations, the distance D2 may be within the range of about one micron to about 10 microns. In some instances, the distance D2 may be large enough to protect the distal end 318 of the optical fiber 314, which may be fragile, while small enough provide a wide illumination angle θ as shown in FIG. 2. Accordingly, the cannula device 300 may provide desired illumination during a procedure, while protecting the distal end 318 of the optical fiber 314 from damage such as during insertion or manipulation of the cannula device 300.

Figure 4:
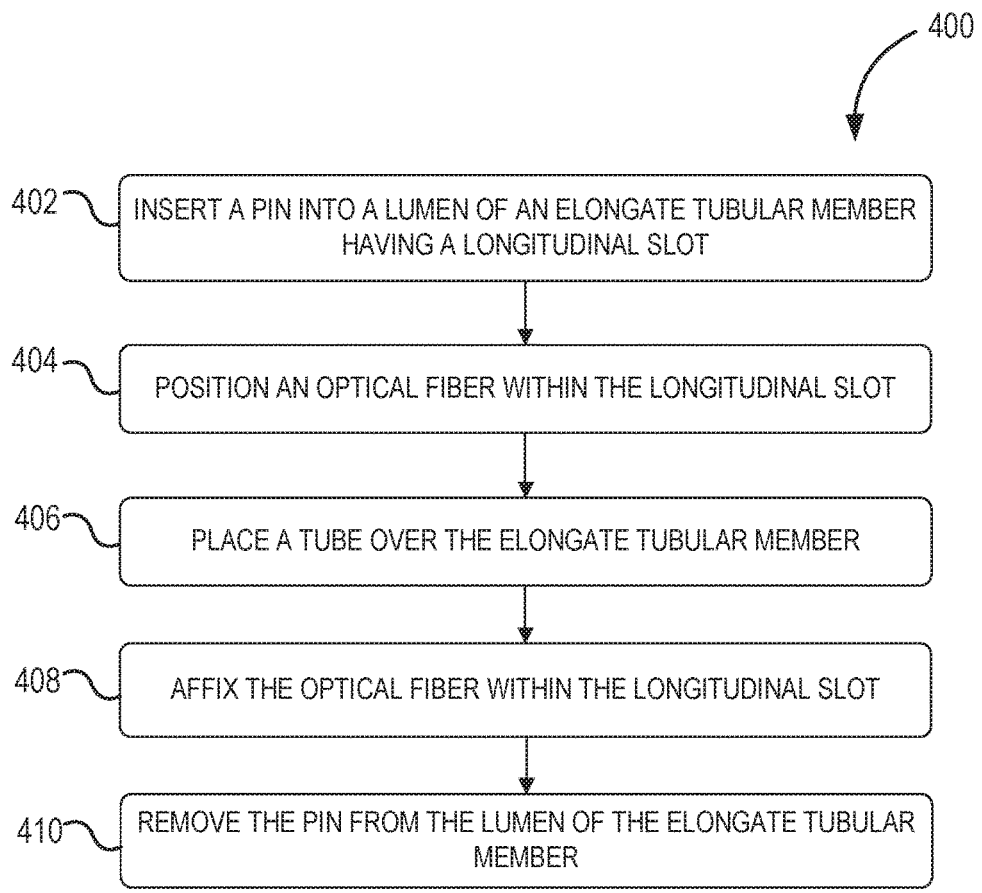
FIG. 4 is an exemplary method of forming a cannula with an integrated illumination device.

FIG. 4 shows an example method 400 of fabricating a cannula device operable to provide illumination, such as, for example, the cannula device 300 described herein. As illustrated in FIG. 4, the method 400 includes several steps or operations undertaken to produce or fabricate a cannula device. Implementations of the method 400 may include additional operations before, after, in between, or as part of the enumerated operations shown in FIG. 4. Additionally, some implementations of the method 400 may omit one or more of the enumerated operations and/or may include alternative operations. In describing implementations of the method 400, reference is made herein to FIGS. 5, 6A, 7A, 8A, 9A, and 10A, which are perspective views of an example cannula during a fabrication process, and to FIGS. 6B, 7B, 8B, 9B, and 10B, which are end views corresponding to FIGS. 6A, 7A, 8A, 9A, and 10A, respectively.

Figure 5:
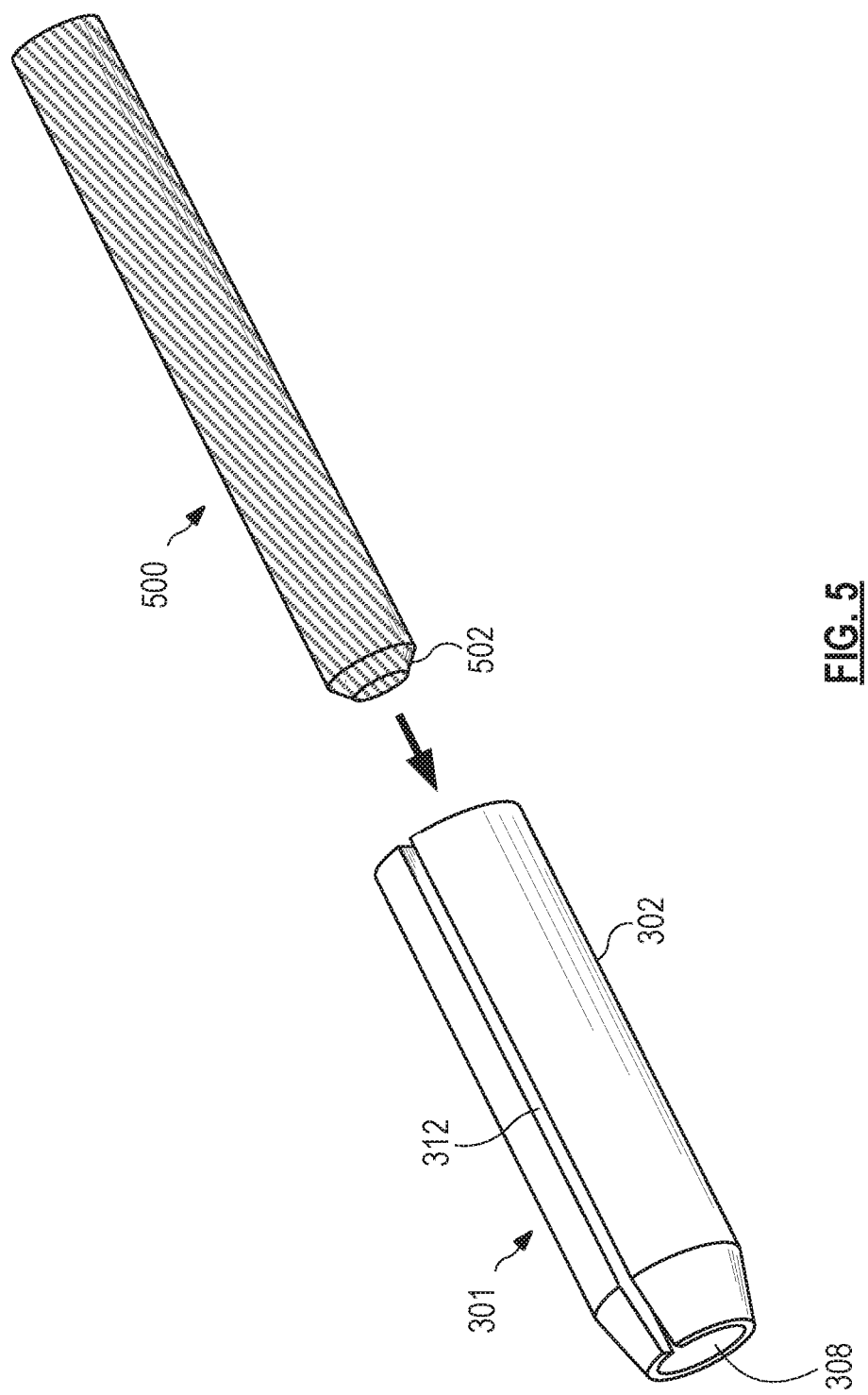
FIGS. 5, 6A, 7A, 8A, 9A, and 10A are perspective views of an exemplary cannula during several operations of fabrication.

At 402, a pin, such as pin 500 shown in FIG. 5, is inserted into the lumen 308 of the elongate tubular member 302 having a longitudinal slot 312 formed therein. However, while a particular example shown in the referenced figures is used, the scope of the disclosure, and method 400 in particular, is not intended to be limited to the example cannula device illustrated. Rather, in the context of method 400, the example cannula device is used merely as an illustrative aid for describing the method 400.

In some implementations, the pin may be inserted into the lumen on an elongate tubular member prior to the formation of the longitudinal slot. FIG. 5 shows a pin 500 being inserted into the lumen 308 of the elongate tubular member 302. The pin 500 may have a non-stick coating formed thereon. For example, the coating of the pin 500 may be formed from polytetrafluoroethylene (PTFE). The non-stick coating of the pin 500 may facilitate the insertion and removal of the pin 500 from the lumen 308 during fabrication. The diameter of the lumen 308 may be substantially identical to the outer diameter of the pin 500 such that there are substantially no gaps are formed between the pin 500 and the inner surface 309 of the elongate tubular member 302. The pin 500 may be formed from a rigid material. For example, the pin may be formed from a metal, such as steel, brass, aluminum, or titanium; a polymer; or any other rigid material. Further, the pin may be formed from a biocompatible material. In some particular implementations, the pin may be formed from stainless steel or another biocompatible metal or a biocompatible polymer. In some implementations, the pin 500 may include a distal tapered section 502. The distal tapered section 502 may facilitate alignment of the pin 500 with the lumen 308 of the elongate tubular member 302 for insertion therein.

Figure 6:
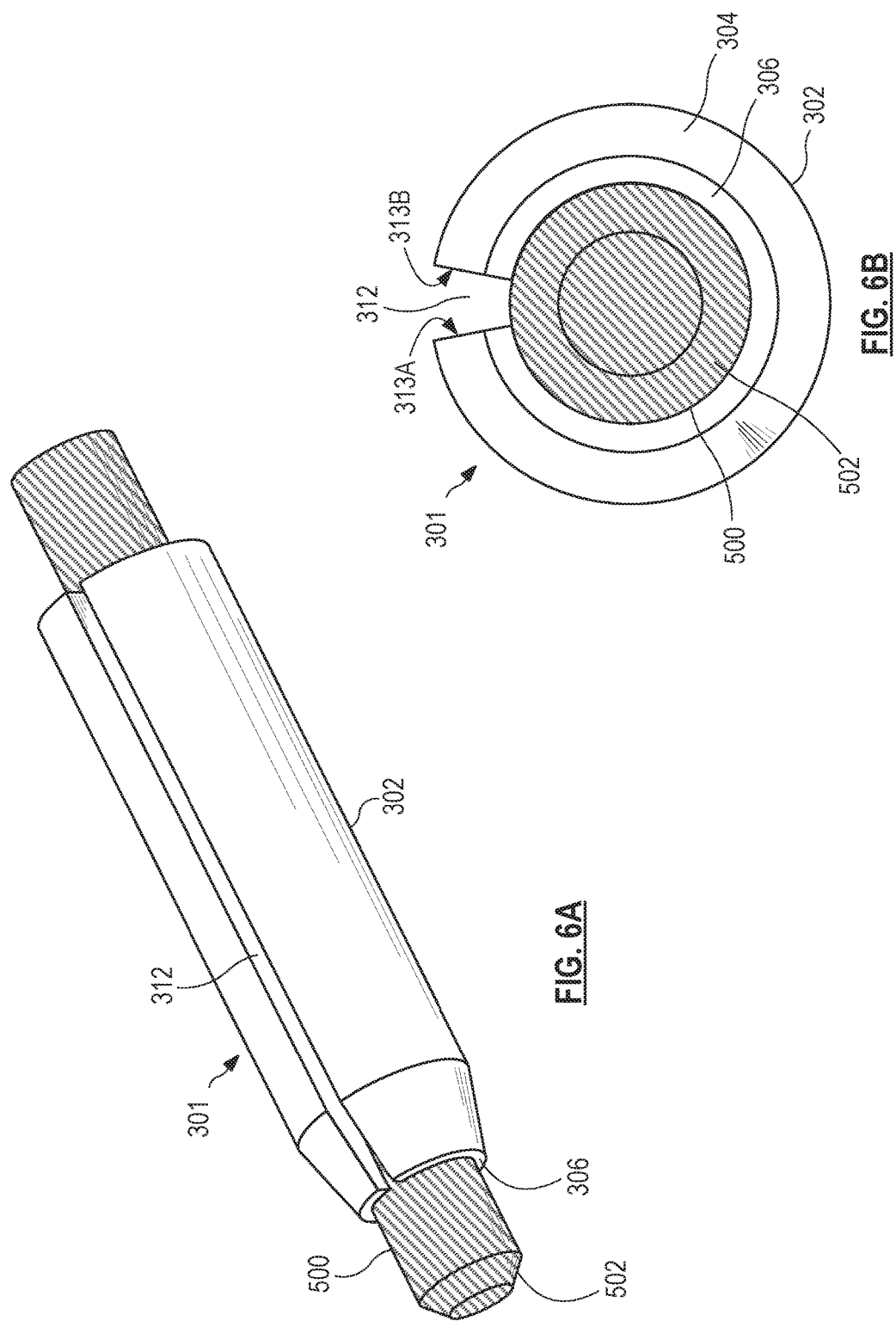
FIGS. 6B, 7B, 8B, 9B, and 10B are end views of the exemplary cannula during fabrication as seen in FIGS. 6A, 7A, 8A, 9A, and 10A, respectively.

Referring now to FIGS. 6A and 6B, the pin 500 is shown disposed within the lumen 308 of the elongate tubular member 302. The pin 500 is positioned within the lumen 308 such that the distal end of the pin 500, including the distal tapered section 502, protrudes beyond the distal end 306 of the elongate tubular member 302.

Figure 7:
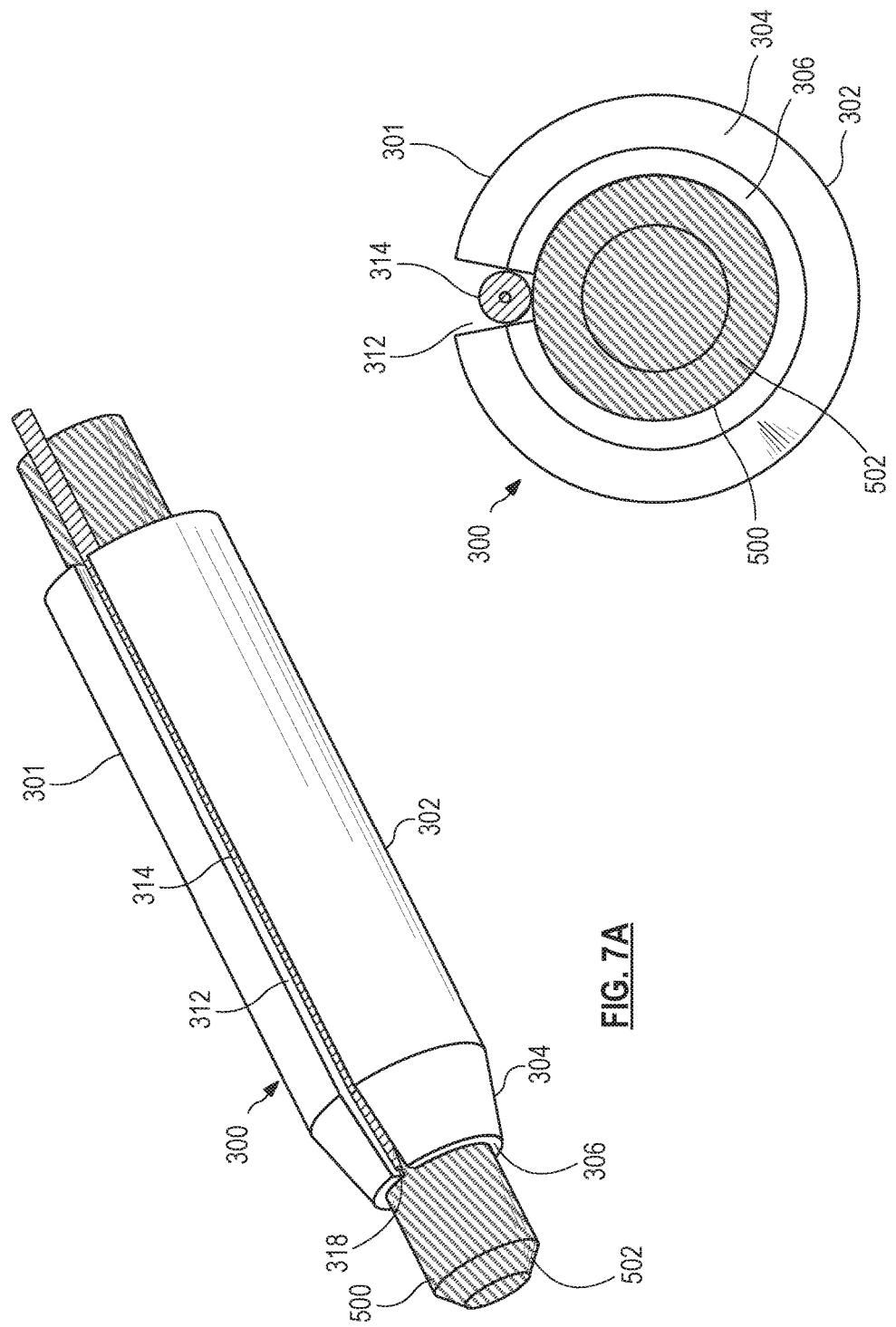

At 404 of FIG. 4, an optical fiber is positioned within the longitudinal slot 312. As shown in FIGS. 7A and 7B, the optical fiber 314 may be positioned within the longitudinal slot 312 of the elongate tubular member 302. The optical fiber 314 is inserted into the longitudinal slot 312 and may be positioned in contact with the pin 500. In some instances, the optical fiber 314 may extend within only a portion of the longitudinal slot 312. In other instances, the optical fiber 314 may extend within the entire length of the longitudinal slot 312. The distal end 318 of the optical fiber 314 may be positioned within the longitudinal slot 312 such that the distal end 318 of the optical fiber 314 is offset from the distal end 306 of the elongate tubular member 302. The offset between the distal end 318 of the optical fiber 314 and the distal end 306 of the elongate tubular member 301 may protect the optical fiber 314 from damage, such as breakage, upon contact with body tissues or other physical contact. For example, the distal end 318 of the optical fiber 314 may be offset from a distal end 306 of the elongate tubular member 302 by the distance D2 shown in FIG. 3D. In some implementations, the distal end 318 of the optical fiber 314 may be offset from the distal end 306 of the elongate tubular member 302 by a distance ranging from about 1 to about 10 microns. However, this offset range is provided merely as an example, and it is within the scope that any desired offset between the distal end 318 of the optical fiber 314 and the distal end 306 of the elongate tubular member 302 may be used.

Figure 8:
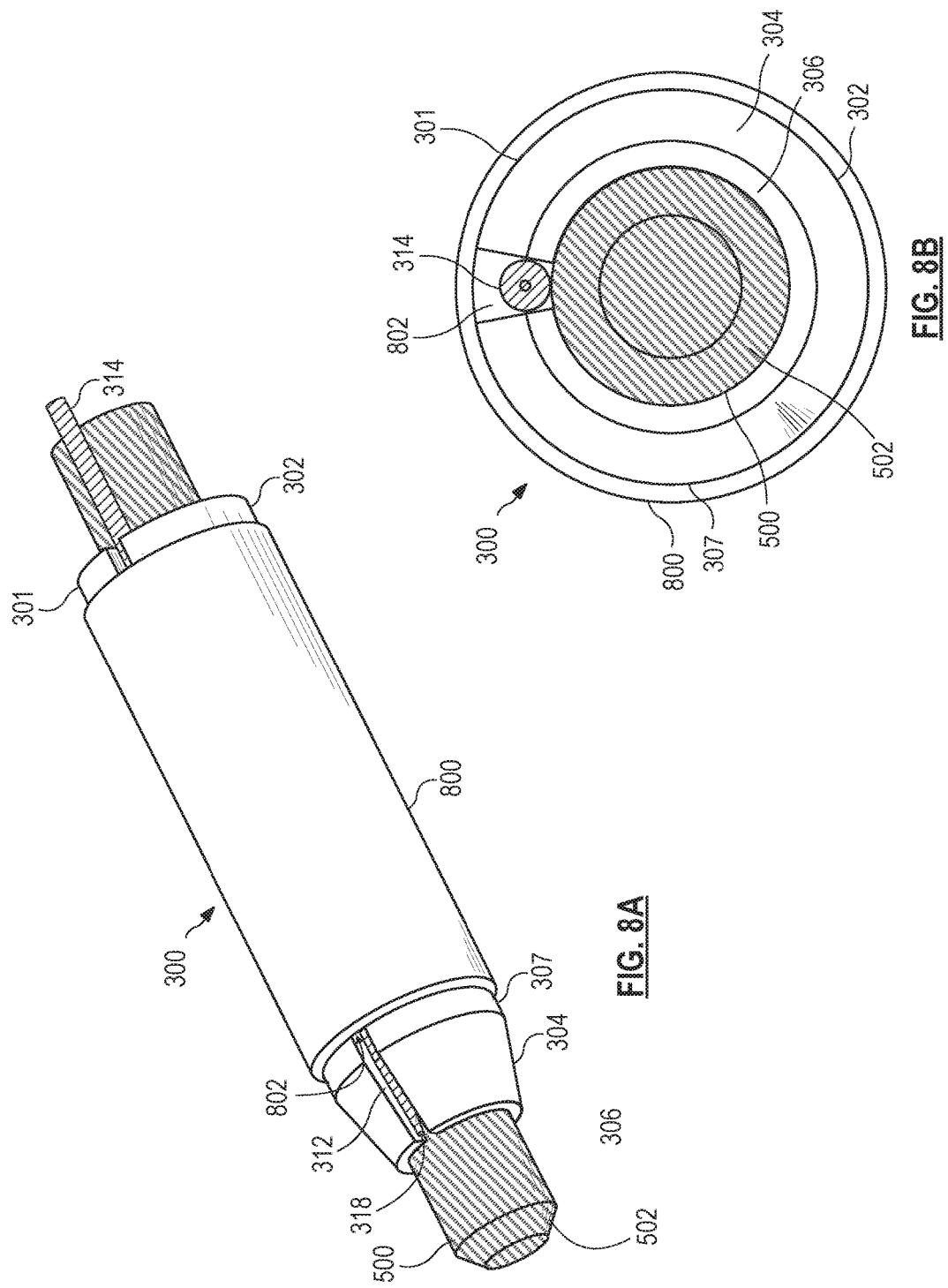

At 406, a tube 800 may be placed over the elongate tubular member 302, as illustrated in FIGS. 8A and 8B. The tube 800 may form a channel 802 defined by the longitudinal slot 312, the outer surface of the pin 500, and an interior surface of the tube 800. The channel 802 may extend at least partially along a length of the elongate tubular member 302. The channel 802 contains at least a portion of the optical fiber 314. An adhesive may be inserted into the channel 802 to affix the optical fiber 314 within the longitudinal slot 312.

FIG. 8A illustrates that when the pin 500 is positioned within the lumen 308 of the elongate tubular member 302, tube 800 is positioned thereover, such that the tube 800 surrounds a portion of the elongate tubular member 302 and a portion of the pin 500. In some implementations, the tube 800 may be a flexible tube and may be shorter in length than the cylindrical section of the elongate tubular member 302 as illustrated in FIG. 8A. In other implementations, a portion of the tube 800 may extend over the tapered section 304 of the elongate tubular member 302. Thus, the tube 800 may extend over along an entire length of the cannula 301 or only a portion thereof. Therefore, while FIG. 8A illustrates the tube 800 extending over less than the entire length of the cannula 301, the scope of the disclosure is not so limited. Rather, the tube 800 may be sized to extend over the entire length of the cannula 301 or only a portion thereof.

The tube 800 may have an inner diameter that corresponds to the outer diameter of the elongate tubular member 302 or may be deformed to have an inner diameter corresponding to the outer diameter to the elongate tubular member 302. That is, in some implementations, a formed inner size or diameter of the tube 800 may be less than the outer size or diameter of the elongate tubular member 302. When the tube 800 is applied to the elongate tubular member 302, the tube 800 may be made to expand thereover and conform to the outer surface of the elongate tubular member 302. For example, the tube 800 may be made from a flexible material in order to facilitate placement over the elongate tubular member 302. In other instances, the inner size or diameter of the tube 800 may be larger than the outside size or diameter of the elongate tubular member 302. For example, the tube 800 may be a heat-shrink tube that contracts when exposed to heat, reducing in size. When the tube 800 is subjected to sufficient heat, the tube 800 may conform to the outer surface 307 of the elongate tubular member 302 such that, aside from the longitudinal slot 312, substantially no gaps are present between the inner surface of the tube 800 and the outer surface 307 of the elongate tubular member 302.

At 408 in FIG. 4, the optical fiber 314 is affixed within the longitudinal slot 312. In some implementations, the tube 800 may contact a length of the optical fiber 314, such that the tube 800 may secure the optical fiber 314 in position. For example, the tube 800 may be positioned over the elongate tubular member 302 and heat may be applied thereto to cause the tube 800 to contract. As the tube 800 contracts, the tube 800 may secure the optical fiber 314 within the longitudinal slot 312.

Figure 9:
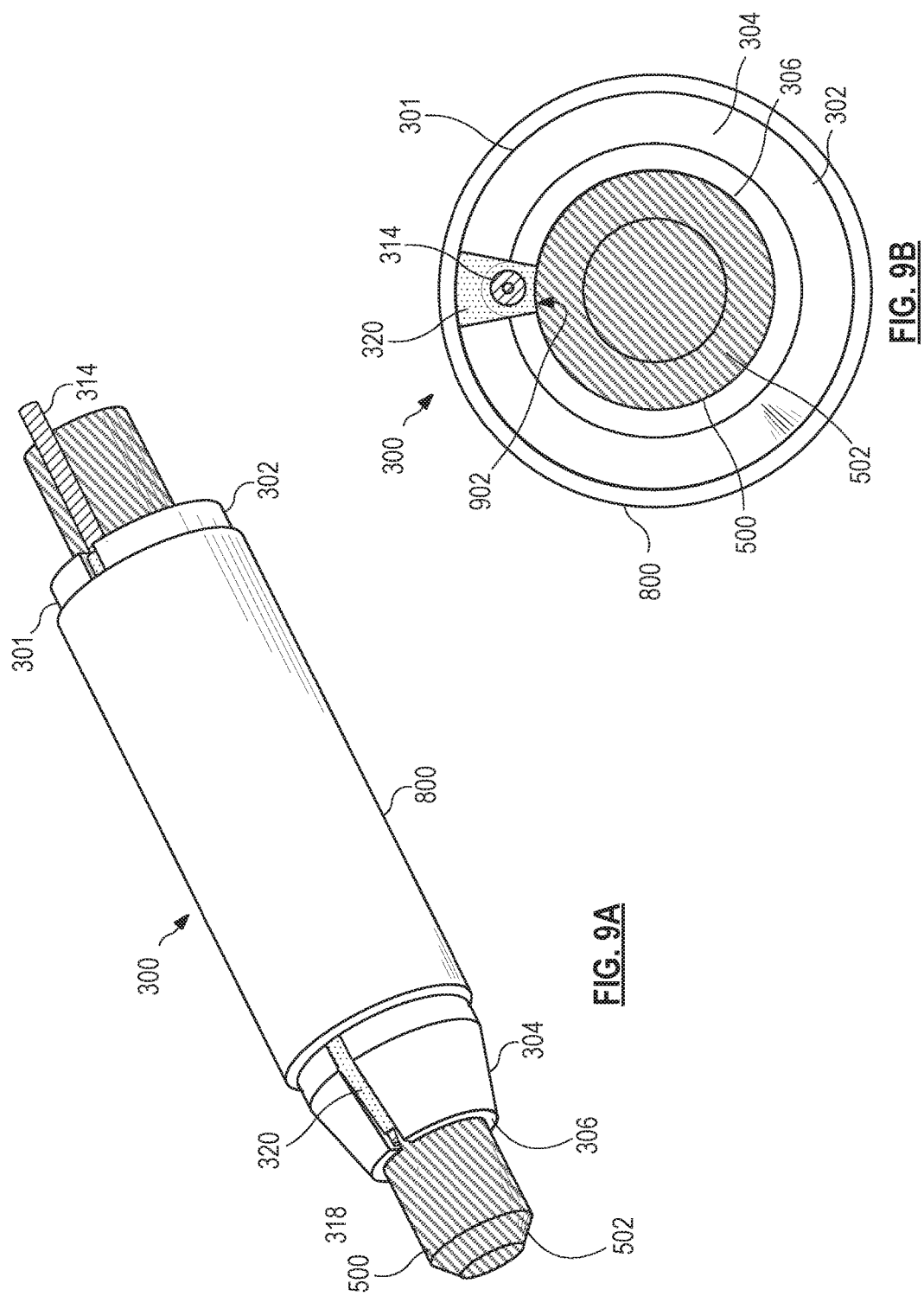

FIGS. 9A and 9B show a perspective view and an end view of the cannula device 300, during fabrication according to an implementation of the method 400. As illustrated, an adhesive 320 may be introduced into the channel 802. For example, an epoxy or other flowable adhesive may be injected into the channel 802 at one end thereof. For example, a flowable adhesive 320 may be injected into the proximal end of the longitudinal slot 312. The adhesive 320 may substantially fill the channel 802. As the adhesive 320 is injected, the adhesive 320 may flow from the proximal end of the longitudinal slot 312 toward the distal end thereof. In some instances, the adhesive 320 may be injected into the distal end of the channel 802 or into both ends of the channel 802. An amount of adhesive 320 introduced into the channel 802 may be selected to fill all or substantially all of the channel 802. In other instances, an amount of adhesive 320 introduced may be sufficient to extend beyond the distal end of the tube 800, as shown, for example, in FIG. 9A.

Introduction of the adhesive 320 may be stopped after a selected volume of adhesive 320 has been introduced. The known volume of the adhesive 320 may be sufficient to secure the optical fiber 314 in position within the longitudinal slot 312, including a portion of the tapered distal section 316, without covering the distal end 318 of the optical fiber 314. The application of the adhesive 320 may be controlled so that adhesive 320 is prevented from flowing over or contacting the distal end 318 of the optical fiber 314. Further, the amount of adhesive 320 that is introduced may be selected so as to provide for the offset distance D1 shown in FIG. 3D. Control of an amount of adhesive introduced into the channel 802 may be important. For example, adhesive 320 that is deposited too close to the distal end 318 of the optical fiber 314 may distort the illumination output therefrom, including the illumination angle θ, shown in FIG. 2, and may also result in thermal damage to the distal end 318 of the optical fiber 314 due to high irradiance at the interface between the distal end 318 of the optical fiber 314 and the adhesive 320.

In some implementations, the adhesive 320 may be a curable adhesive that is to be cured in order to affix the optical fiber 314 within the channel 802. In such implementations, the adhesive 320 may be cured by heat or by exposure to radiation, such as ultraviolet radiation. Where a particular radiation or bandwidth of radiation is used to cure the adhesive 320, the tube 800 may be made of a material that is transparent or substantially to the bandwidth of radiation. For example, some implementations of the tube 800 may be formed from a material that is transparent to ultraviolet radiation.

When the adhesive 320 is cured or hardened, the portion of the adhesive 320 that is in contact with the pin 500 may solidify to form a surface 902 that substantially matches or completes the curvature of the central lumen 308. The adhesive 320 may completely or substantially fill an entire radial thickness of the longitudinal slot 312 along an entire length or a selected portion thereof.

Figure 10:
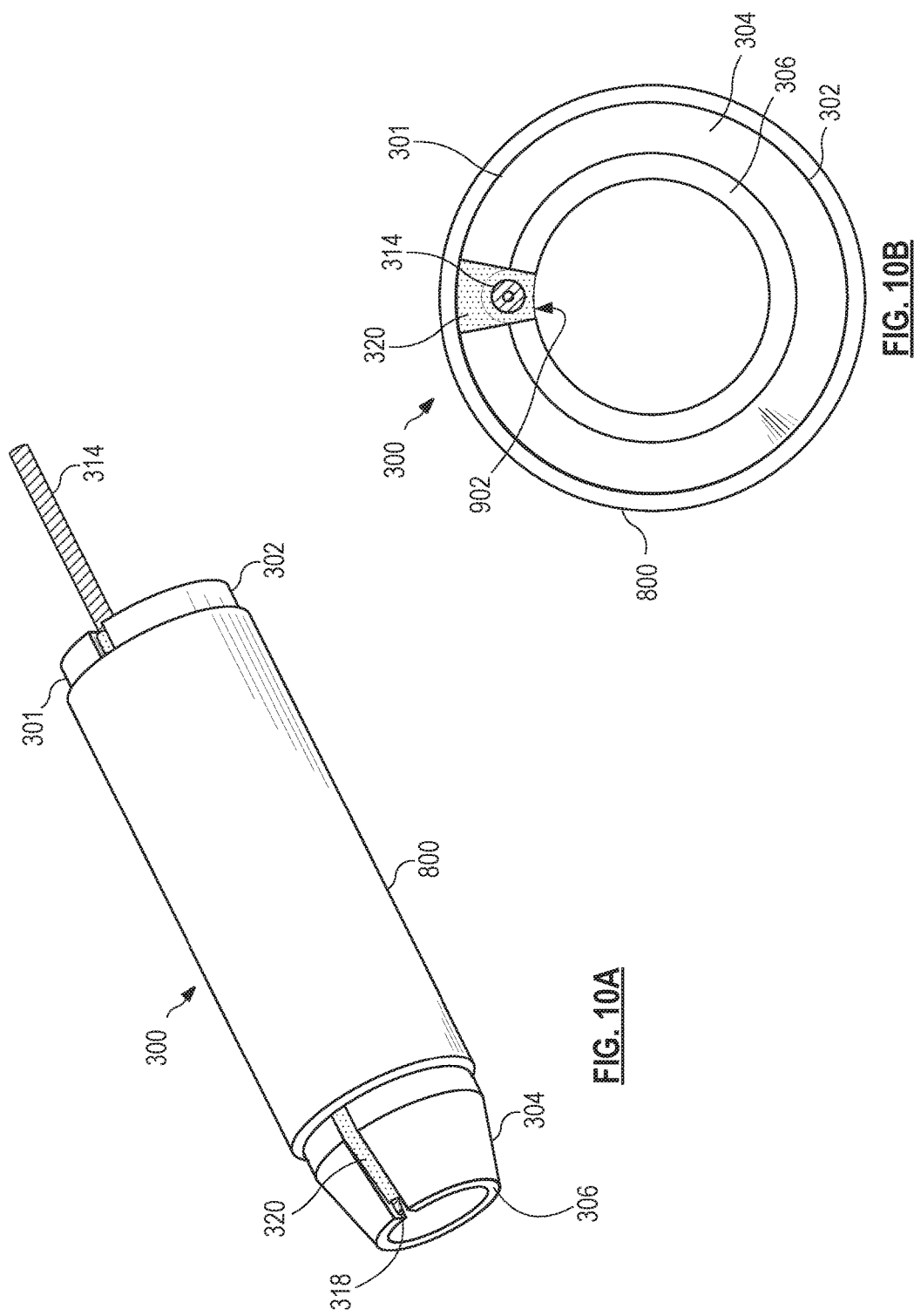

At 410, the pin may be removed from the lumen of the elongate tubular member 302. Referring now to FIGS. 10A and 10B, the pin 500 has been removed from the lumen 308, exposing the surface 902 which substantially corresponds to the interior or inner surface 309 of the lumen 308. Due to the non-stick property of the surface of the pin 500, the pin 500 may be easily removed from the lumen 308 after the curing process of the adhesive 320 is complete. In other implementations, the adhesive 320 may be partially-cured before the pin 500 is removed and then fully-cure or harden after the removal of the pin 500 from the lumen 308. The non-stick coating or material of the pin 500 may facilitate removal from the lumen 308.

Additionally, in some implementations, the tube 800 may be removed as part of the method 400. In some implementations, the tube 800 may be removed prior to the removal of the pin 500. The tube 800 may be removed by axially sliding the tube 800 off of the outer surface 307 of the elongate tubular member 302. In other instances, the tube 800 may be removed by cutting or by another suitable removal process. When the tube 800 is removed, the portion of the adhesive 320 that contacts the tube 800 may form a curved surface that substantially conforms and completes the exterior or outer surface 307 of the elongate tubular member 302.

Figure 11:
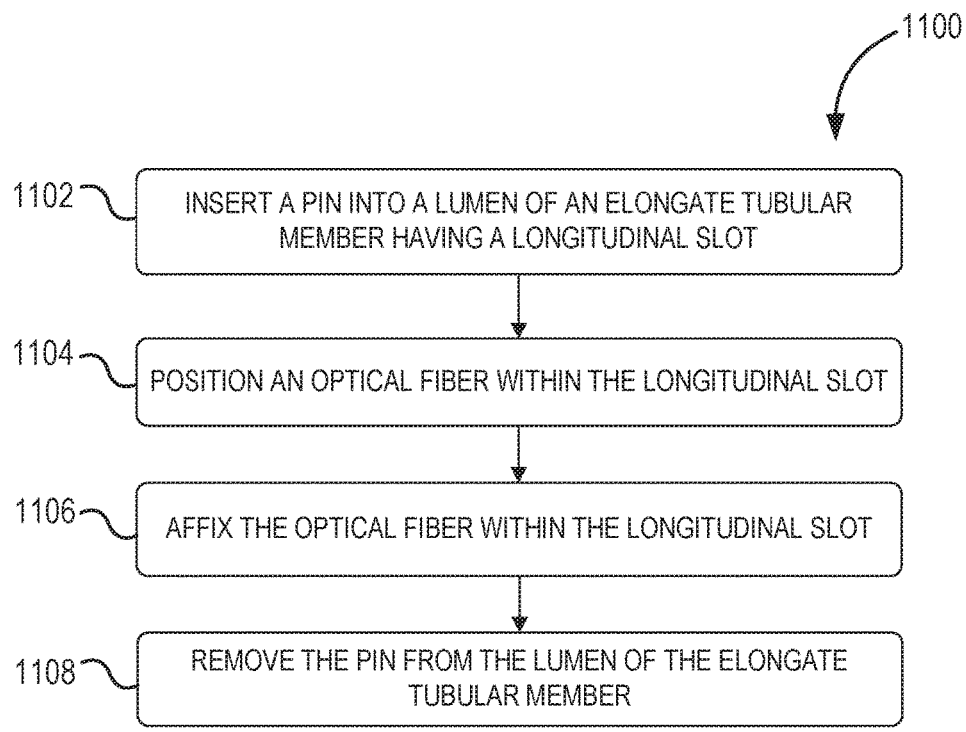
FIG. 11 is another exemplary method of forming a cannula with an integrated illumination device.

Referring now to FIG. 11, shown therein is a method 1100 of fabricating a trocar cannula with an integrated illumination device. Implementations of the method 1100 may include additional operations before, after, in between, or as part of the enumerated operations. The method 1100 is similar in many respects to the method 400 of FIG. 4 as described herein. For example, the method 1100 may begin at 1102, when a pin is inserted into a lumen of an elongate tubular member having a longitudinal slot formed in a wall thereof. For example, the pin 500 may be inserted into the lumen 308 of the elongate tubular member 302 as shown in FIGS. 5, 6A, and 6B. At 1104, an optical fiber may be positioned within the longitudinal slot. For example, the optical fiber 314 may be placed within the longitudinal slot 312 alongside the pin 500. At 1106, the optical fiber may be affixed within the longitudinal slot. For example, the optical fiber 314 may be glued or adhered within the longitudinal slot 312 by an adhesive. The adhesive may be similar to the adhesive 320 described herein in connection with FIGS. 9A, 9B, 10A, and 10B. Consequently, the adhesive may be introduced, such as, for example by injection from a nozzle, along a complete or partial length of the longitudinal slot 312. In some implementations, heat may be applied to lower the viscosity of the adhesive 320, facilitating coverage of the adhesive 320 within the longitudinal slot 312. In such implementations, an inner surface 902 of the adhesive 320 may conform to the interior surface of the lumen 308. At 1108, the pin may be removed from the lumen of the elongate tubular member. For example, the pin 500 may be removed from the lumen 308 by sliding the pin 500 out therefrom, as seen in FIGS. 10A and 10B.

Implementations of the present disclosure may include cannula devices having an integrated illumination component. Methods of fabricating such cannula devices are also described herein. A cannula device having an integrated illumination component, such as, for example, the cannula device 300, may provide for illumination within a body cavity, like a posterior segment of an eye, while decreasing the total number of incisions that need to be made.

Through use of principles described herein, a user is able to achieve a better experience when viewing the surgical site and may be required to form fewer incisions through tissue, such that the surgical procedure may be performed more efficiently. Patients treated using device such as those described herein may be able to recover faster and may suffer fewer complications. Although particular exemplary implementations are described above, the implementations encompassed by the present disclosure are not limited thereto. In that regard, although illustrative implementations have been shown and described, a wide range of modifications, changes, and substitutions is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. A surgical instrument for use in an ophthalmic procedure, the surgical instrument comprising:
an elongate tubular member having a distal end for insertion through eye tissue to provide access to an interior of an eye, the elongate tubular member comprising:
an inner surface;
an outer surface; and
a longitudinally-extending slot extending in a proximal direction from the distal end of the elongate tubular member; and
an optical fiber disposed within the longitudinally-extending slot and affixed to the elongate tubular member within the longitudinally-extending slot.

2. The surgical instrument of claim 1, further comprising a flexible tube disposed around a portion of the elongate tubular member, the flexible tube conforming to an outer surface of the elongate tubular member.

3. The surgical instrument of claim 1, wherein the longitudinally-extending slot in the elongate tubular member extends from the outer surface to the inner surface.

4. The surgical instrument of claim 1, wherein the optical fiber comprises a tapered distal section and a distal end, the tapered distal section of the optical fiber affixed within the longitudinally-extending slot and such that the distal end of the optical fiber is offset from the distal end of the elongate tubular member by approximately 10 microns or less.

5. The surgical instrument of claim 1, wherein the optical fiber is affixed within the longitudinally-extending slot by an ultraviolet radiation curable adhesive and wherein the surgical instrument further comprising a heat-shrink tube disposed around and conforming to a portion of the elongate tubular member, the heat-shrink tube formed of a material that is transparent or substantially transparent to ultraviolet radiation.

6. The surgical instrument of claim 1, wherein the inner surface of the elongate tubular member is a substantially cylindrical surface defining a lumen, and wherein an inner surface of an adhesive affixing the optical fiber within the longitudinally-extending slot has a curvature matching a curvature of the substantially cylindrical surface.

7. The surgical instrument of claim 1, wherein opposing walls of the longitudinally-extending slot in the elongate tubular member are parallel.

8. A method of forming a surgical instrument, the method comprising:
inserting a pin into a lumen extending through an elongate tubular member comprising a wall that defines an inner surface and an outer surface, the inner surface defining an inner diameter, an outer diameter of the pin substantially matching the inner diameter of the elongate tubular member;
positioning an optical fiber within a longitudinal slot formed in the elongate tubular member, the longitudinal slot extending through the wall of the elongate tubular member from the outer surface to the inner surface;
affixing the optical fiber within the longitudinal slot; and
removing the pin from the lumen of the elongate tubular member.

9. The method of claim 8, further comprising:
positioning a flexible tube around the elongate tubular member; and
causing the flexible tube to conform to an outer surface of the elongate tubular member.

10. The method of claim 8, wherein affixing the optical fiber within the longitudinal slot further comprises:
applying an adhesive within the longitudinal slot; and
curing the adhesive.

11. The method of claim 10, wherein curing the adhesive comprises at least one of: applying heat to the adhesive and exposing the adhesive to ultraviolet radiation.

12. The method of claim 10, wherein applying the adhesive within the longitudinal slot comprises injecting a volume of the adhesive into a channel defined by an outer surface of the pin, an inner surface of a flexible tube that conforms to an outer surface of the elongate tubular member, and opposing walls of the longitudinal slot.

13. The method of claim 8, wherein an outer surface of the pin comprises a non-stick material.

14. The method of claim 8, wherein the pin is formed from a PTFE material.

15. The method of claim 8, further comprising forming the longitudinal slot in the elongate tubular member by laser cutting, milling, or electrical discharge machining.

16. A method of forming a trocar cannula for use in an ophthalmic surgical procedure, the method comprising:
inserting a pin into a lumen extending through an elongate tubular member, the elongate tubular member comprising a longitudinal slot formed therein;
positioning an optical fiber within the longitudinal slot;
placing a tube over the elongate tubular member;
affixing the optical fiber within the longitudinal slot; and
removing the pin from the lumen of the elongate tubular member.

17. The method of claim 16, wherein affixing the optical fiber comprises injecting a volume of an adhesive into a channel defined by an outer surface of the pin, an inner surface of a flexible tube that conforms to an outer surface of the elongate tubular member, and opposing walls of the longitudinal slot.

18. The method of claim 17, wherein the injected volume of adhesive is such that a most distal portion of the adhesive is offset from a tip of the optical fiber.

19. The method of claim 16, wherein a wall of the elongate tubular member has a thickness of less than about 40 microns, and the optical fiber has a diameter ranging from about 30 microns to about 40 microns.

20. The method of claim 16, wherein positioning the optical fiber within the longitudinal slot comprises placing the optical fiber so that a distal end of the optical fiber is offset from a distal end of the elongate tubular member by approximately 10 microns or less.

* * * * *